(12) United States Patent
Tanimoto et al.

(10) Patent No.: US 9,958,400 B2
(45) Date of Patent: May 1, 2018

(54) PILL INSPECTION APPARATUS AND PILL INSPECTION METHOD

(71) Applicant: PANASONIC HEALTHCARE HOLDINGS CO., LTD., Tokyo (JP)

(72) Inventors: Takanobu Tanimoto, Tokyo (JP); Hitoshi Yamashita, Tokyo (JP); Hiroshi Ehara, Tokyo (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 28 days.

(21) Appl. No.: 14/892,870

(22) PCT Filed: Apr. 9, 2014

(86) PCT No.: PCT/JP2014/002042
§ 371 (c)(1),
(2) Date: Nov. 20, 2015

(87) PCT Pub. No.: WO2014/188650
PCT Pub. Date: Nov. 27, 2014

(65) Prior Publication Data
US 2016/0109385 A1    Apr. 21, 2016

(30) Foreign Application Priority Data

May 22, 2013  (JP) ................................ 2013-107641

(51) Int. Cl.
*G01N 21/95* (2006.01)
*A61J 1/03* (2006.01)
(Continued)

(52) U.S. Cl.
CPC ............ *G01N 21/9508* (2013.01); *A61J 1/03* (2013.01); *G01N 21/8851* (2013.01); *A61J 1/035* (2013.01);
(Continued)

(58) Field of Classification Search
CPC ............. A61K 9/5192; G01N 33/6893; G01N 2021/845; G01N 2021/8841;
(Continued)

(56) References Cited

U.S. PATENT DOCUMENTS 6,450,664 B1 *  9/2002  Kelly ..................... F21V 5/045
                                                       362/218
6,624,885 B1 *  9/2003  Pon ..................... G01N 21/8851
                                                       356/237.6
(Continued)

FOREIGN PATENT DOCUMENTS

EP    1 089 069 A2    4/2001
EP    2 390 656 A2    11/2011
(Continued)

OTHER PUBLICATIONS

International Search Report dated Jun. 10, 2014, issued in counterpart application No. PCT/JP2014/002042 (1 page).
(Continued)

*Primary Examiner* — Kara E Geisel
*Assistant Examiner* — Violeta A Prieto
(74) *Attorney, Agent, or Firm* — Westerman, Hattori, Daniels & Adrian, LLP

(57) ABSTRACT

A pill inspection apparatus of the present invention includes: an illumination portion 30 for irradiating light to a medical envelope 20 in which at least a translucent pill 22 is enclosed; an imaging portion 11 for acquiring a transmission image of the irradiated medical envelope 20; and an image processing portion 12 for detecting, as the translucent pill 22, a pill having a brightness value of its outer periphery lower than that of its center using the transmission image, the illumination portion 30 includes a light emitting portion 31, and a light-collecting portion 33 for collecting light is provided between the light emitting portion 31 and the
(Continued)

medical envelope 20. By obtaining a uniform outline of the translucent pill 22 irrespective of a shooting position, it is possible to inspect the translucent pill 22 irrespective of a permeation rate.

16 Claims, 9 Drawing Sheets

(51) Int. Cl.
    *G01N 21/88*     (2006.01)
    *G01N 21/84*     (2006.01)

(52) U.S. Cl.
    CPC ..... *A61J 2205/40* (2013.01); *G01N 2021/845* (2013.01); *G01N 2021/8841* (2013.01)

(58) Field of Classification Search
    CPC ... G01N 21/9508; G01N 21/8851; A61J 1/03; A61J 1/035
    USPC .................. 356/73, 443–448; 382/128–143; 250/339.01–339.15
    See application file for complete search history.

(56) References Cited

U.S. PATENT DOCUMENTS

| | | | |
|---|---|---|---|
| 2003/0151735 A1* | 8/2003 | Blumenfeld | G01N 21/6428 356/73 |
| 2004/0070754 A1* | 4/2004 | Schuster | G01N 21/8851 356/237.6 |
| 2007/0019186 A1 | 1/2007 | Sung et al. | |
| 2010/0328669 A1 | 12/2010 | Myrick et al. | |
| 2012/0200596 A1 | 8/2012 | Gotou et al. | |
| 2013/0058550 A1* | 3/2013 | Tanimoto | G01N 21/9508 382/128 |
| 2013/0170732 A1* | 7/2013 | Gotou | G01N 21/9508 382/141 |
| 2013/0188038 A1 | 7/2013 | Takanobu et al. | |
| 2013/0282159 A1* | 10/2013 | Morioka | G01N 21/9508 700/109 |
| 2013/0286386 A1* | 10/2013 | Serikawa | G01N 21/9501 356/237.5 |

FOREIGN PATENT DOCUMENTS

| | | | |
|---|---|---|---|
| JP | 56-057939 A | 5/1981 | |
| JP | H05-215908 A | 8/1993 | |
| JP | 2004-234132 A | 8/2004 | |
| JP | 2006-292419 A | 10/2006 | |
| JP | 2008-18230 A | 1/2008 | |
| JP | 2010-86257 A | 4/2010 | |
| JP | 2010-117331 A | 5/2010 | |
| JP | 2010-172672 A | 8/2010 | |
| JP | 2012-078265 A | 4/2012 | |
| JP | 2013088338 A * | 5/2013 | G01N 21/8806 |
| WO | 2013/008392 A1 | 1/2013 | |
| WO | 2013/058360 A1 | 4/2013 | |

OTHER PUBLICATIONS

Extended (Supplementary) European Search Report dated Apr. 19, 2016, issued in counterpart European Patent Application No. 14801582.9. (10 pages).

Office Action dated Dec. 12, 2017, issued in counterpart Japanese Application No. 2015-518055, with English translation (7 pages).

\* cited by examiner

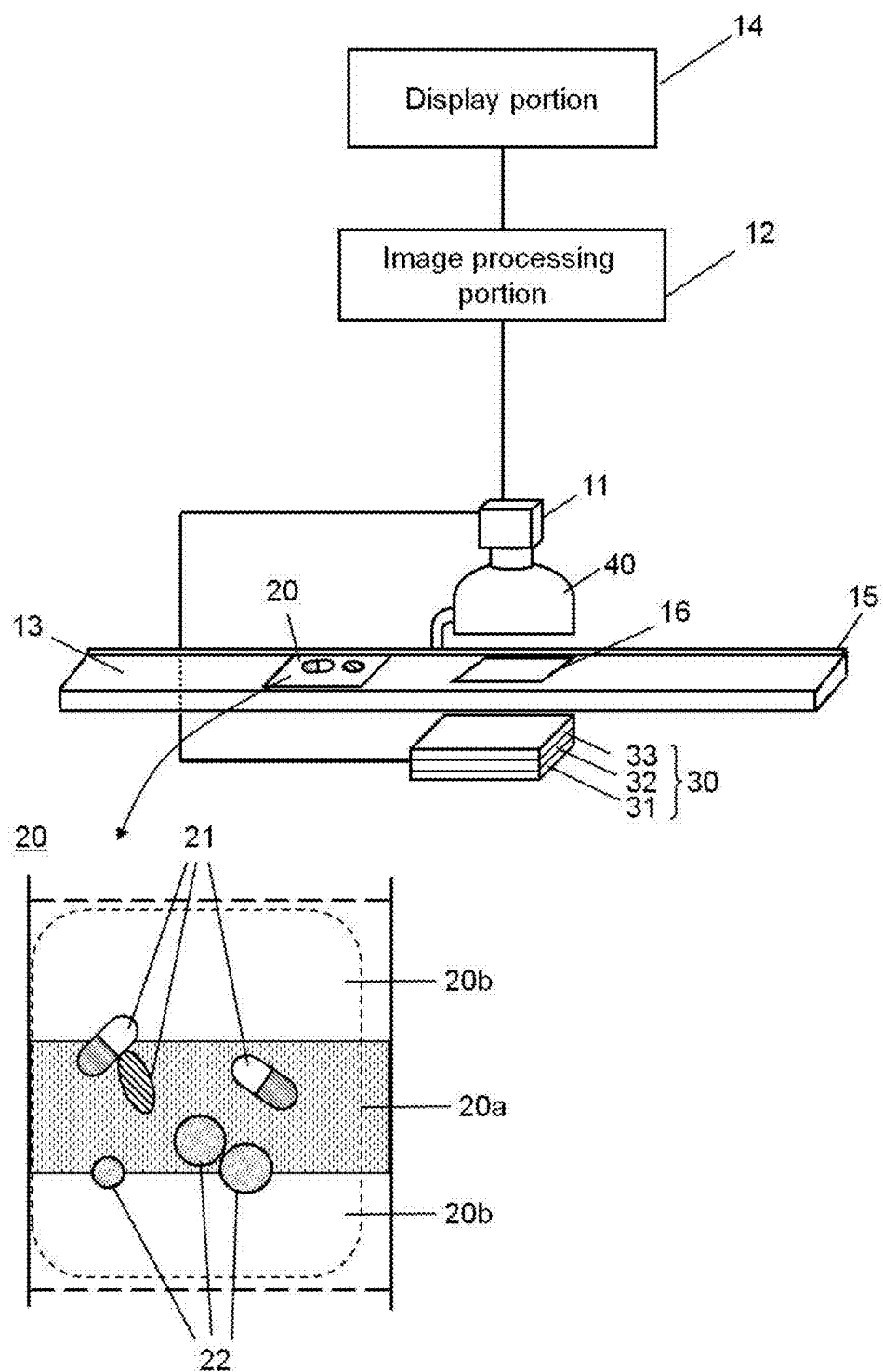

[Fig. 2]
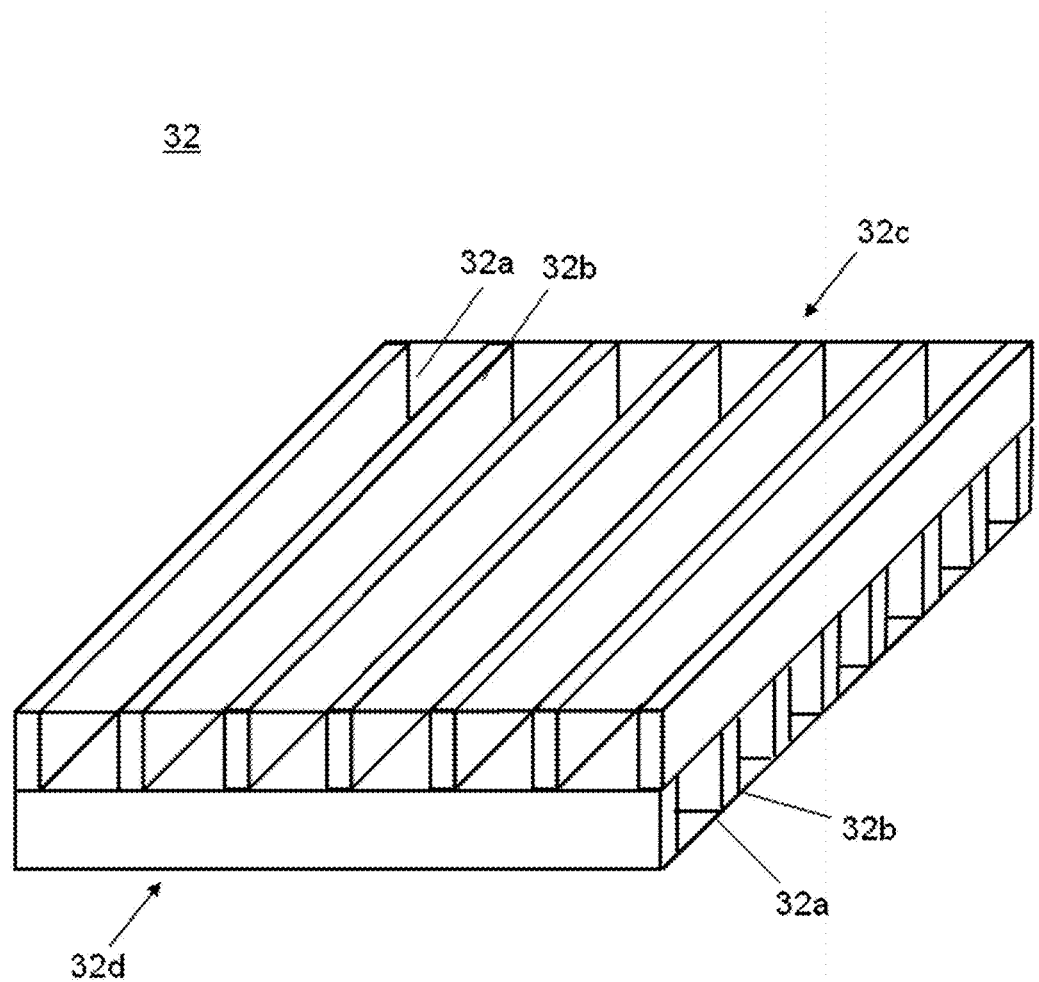

[Fig. 3]
(a)
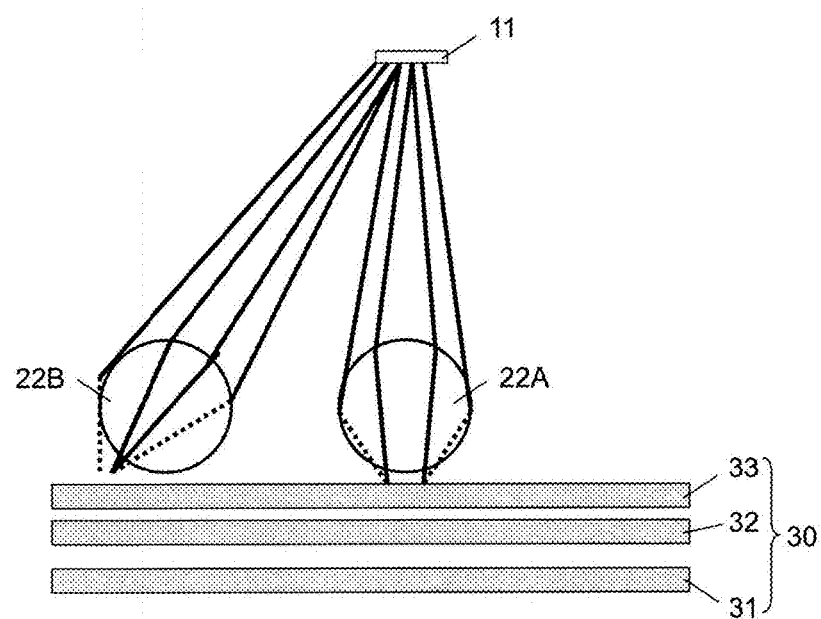
(b)
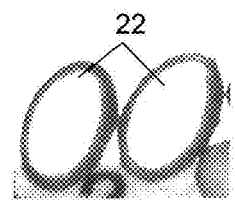

[Fig. 4]
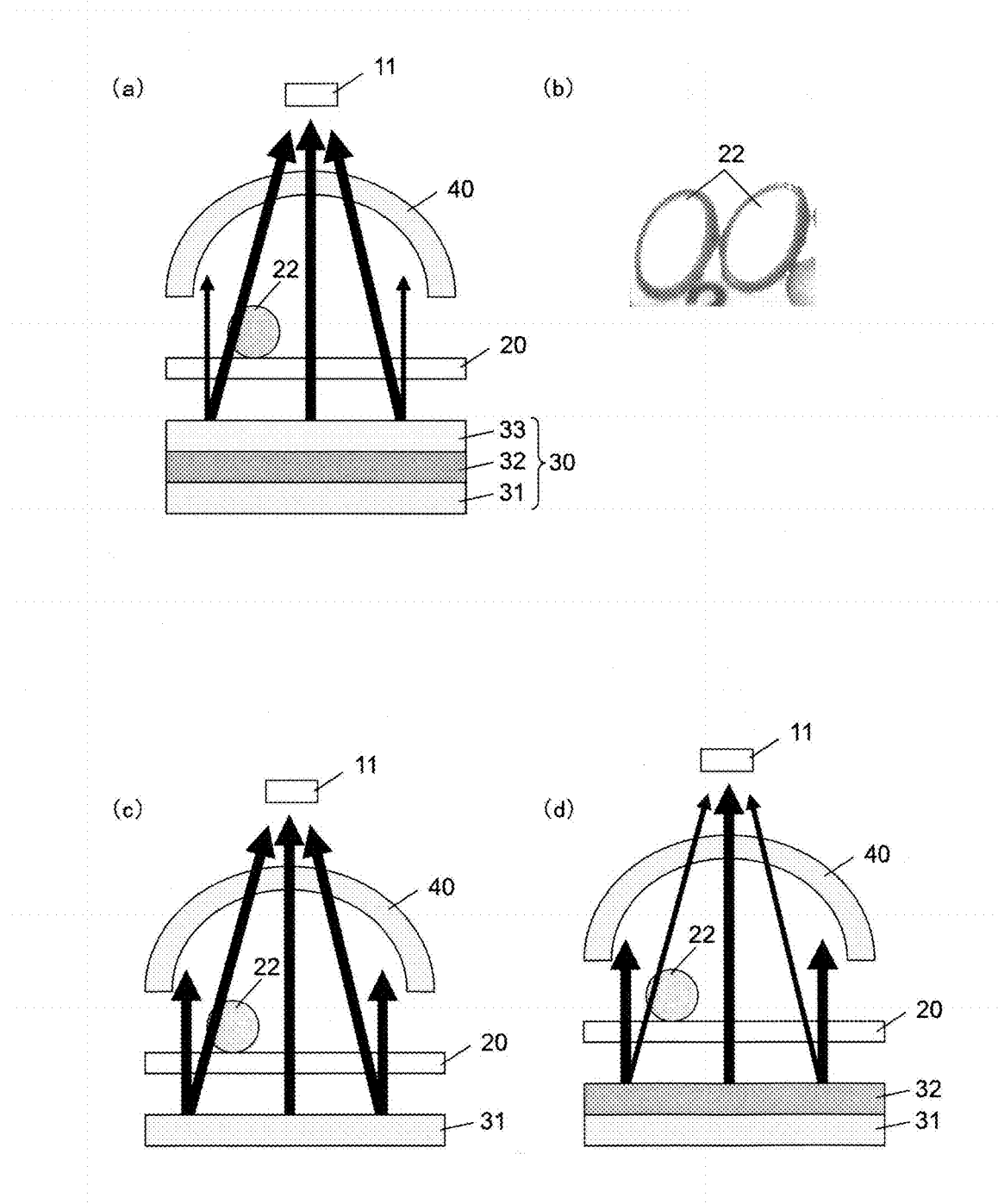

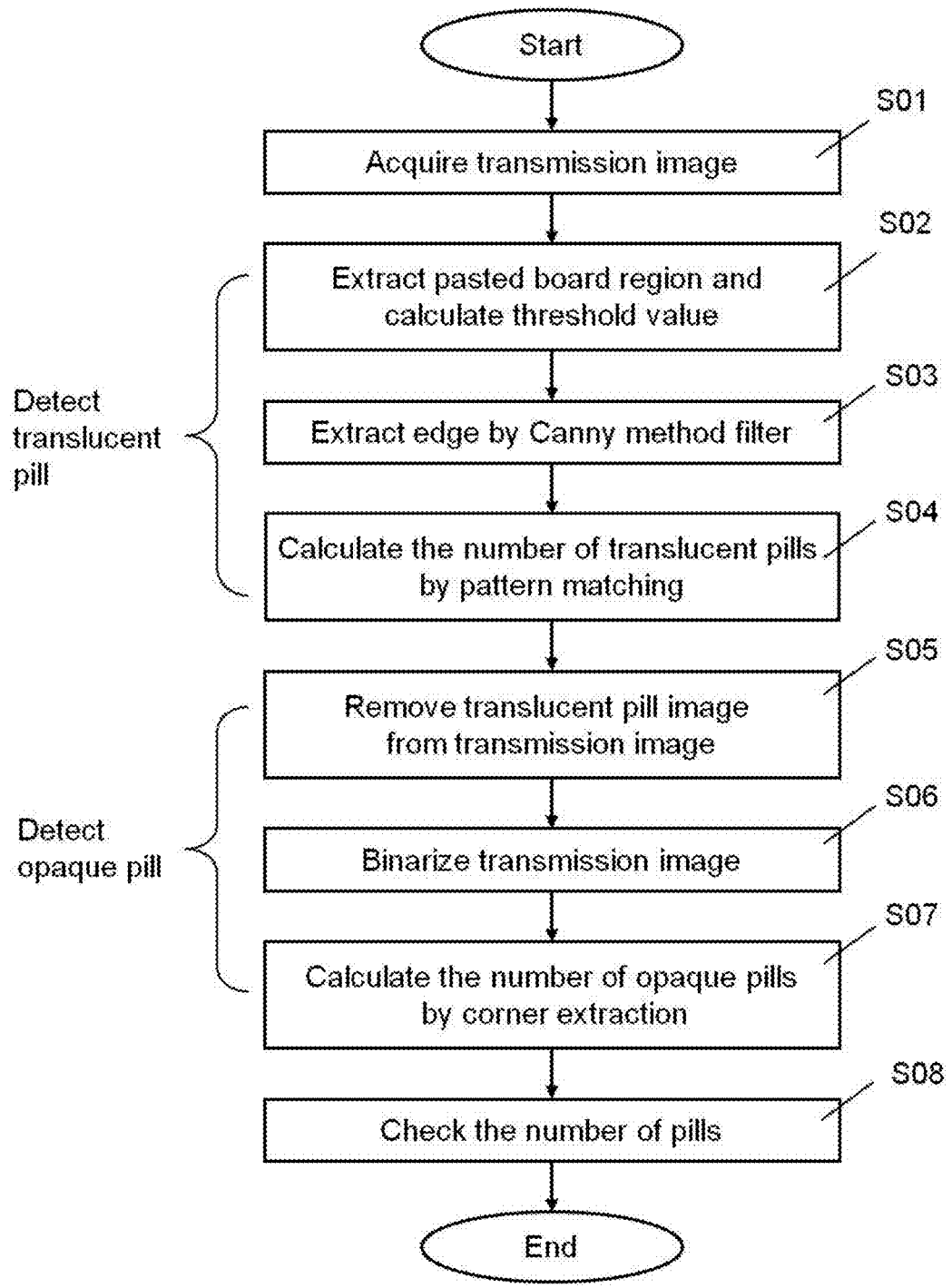
[Fig. 5]

[Fig. 6]
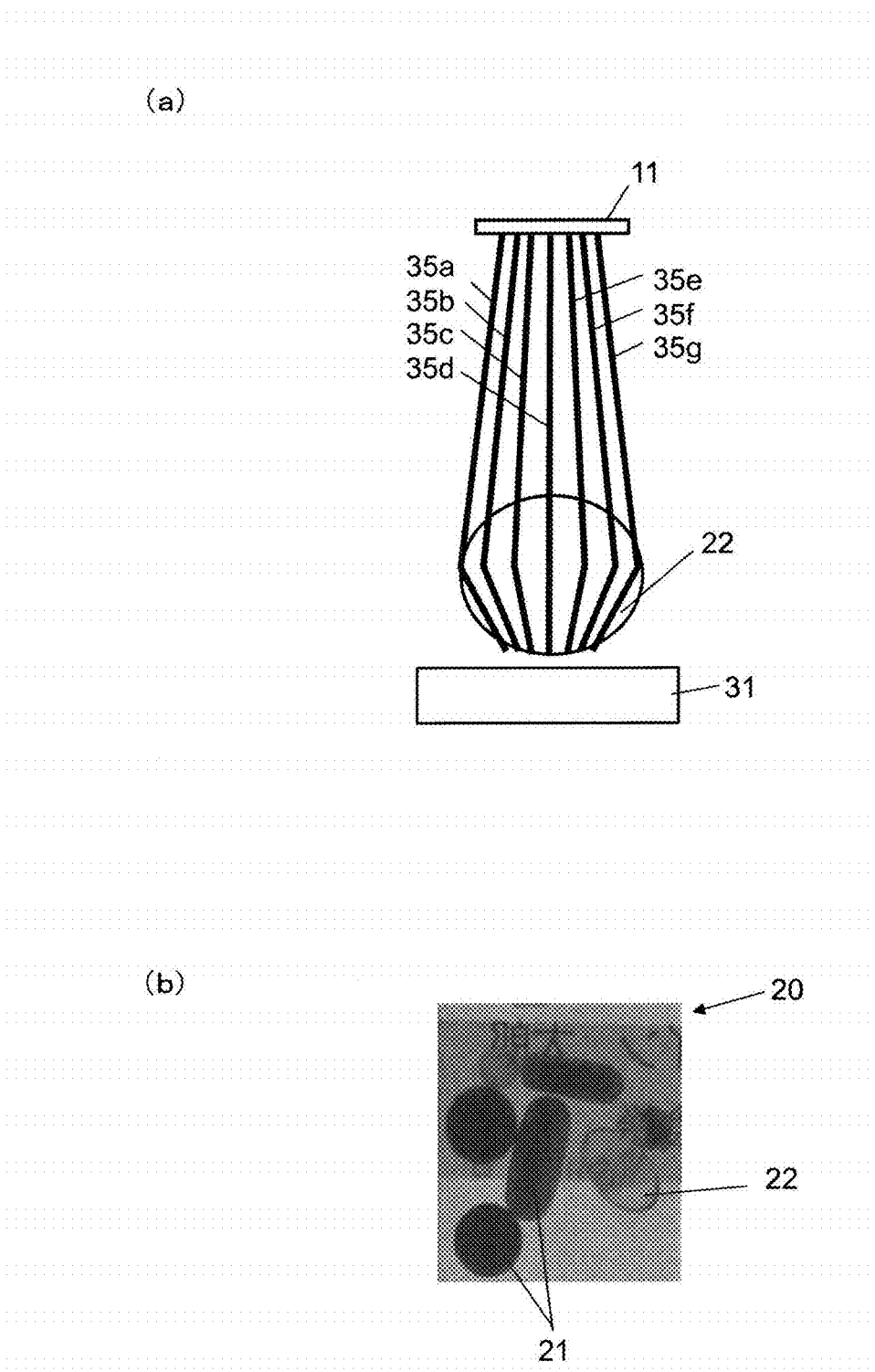

[Fig. 7]
(a)
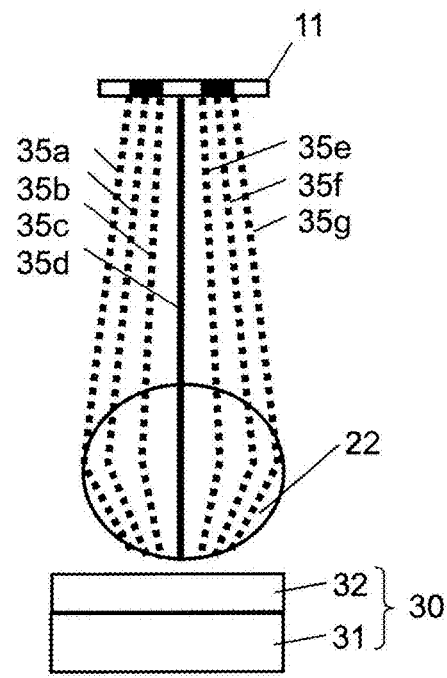
(b)
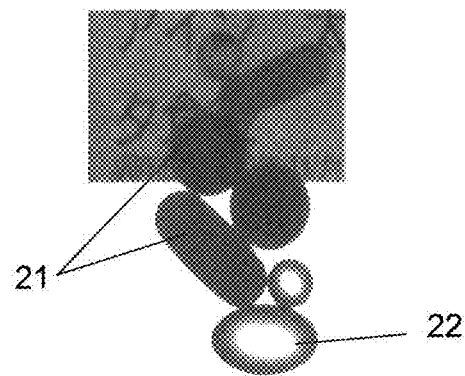

[Fig. 8]
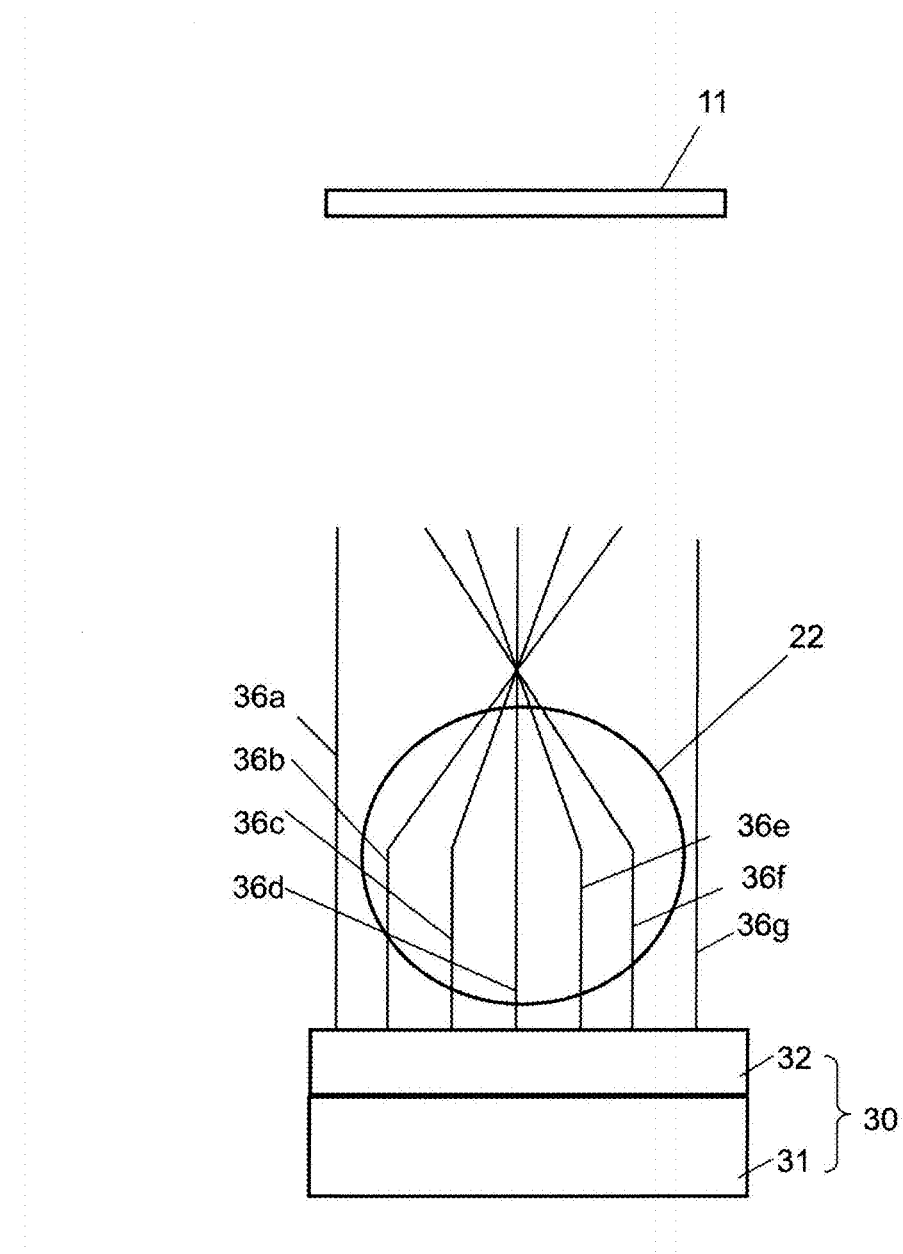

[Fig. 9]
(a)
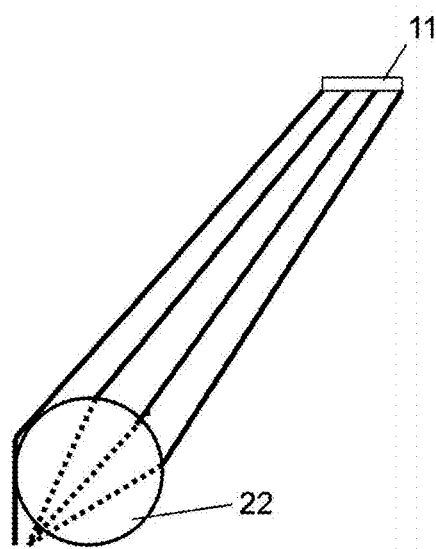
(b)
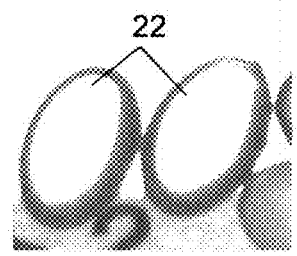

PILL INSPECTION APPARATUS AND PILL INSPECTION METHOD

TECHNICAL FIELD

The present invention relates to a pill inspection apparatus and a pill inspection method for inspecting a pill enclosed in a medical envelope.

BACKGROUND TECHNIQUE

In a hospital and a pharmacy, it is necessary to precisely prepare a medicine based on a prescription. Hence, inspection of preparation of a medicine is carried out after the medicine is prepared. As the preparation operation of a medicine, a pill packaging machine first carries out a packaging operation for packaging different kinds of pills in a medical envelope which is a medical bag. As the inspection of preparation of a medicine, a pill inspection apparatus takes an image of the medical envelope and binarizes the shot images (taken pictures) and then, counts the number of pills existing in the binarized image, and inspects the pills.

As pills, there are translucent pills through which light can pass and opaque pills which block light.

Permeation rates of the translucent pills vary depending upon their kinds, and brightness values of the translucent pills on their images are also different from each other. Depending upon kinds of the translucent pills, brightness value distribution of translucent pills partially overlap brightness value distribution of a back ground. Therefore, it is difficult to precisely carry out the inspection.

FIG. 6 show a conceptual diagram and a shot image of transmission of a translucent pill when diffusion light is used as illumination.

As shown in FIG. 6(a), light which can be received by an imaging portion 11 is limited to light which moves along lines 35a, 35b, 35c, 35d, 35e, 35f and 35g. Light which passes through centers of translucent pills 22 straightly travels along the line 35d, and as the light comes close to an outer peripheral portion in the order of the lines 35c, 35b and 35a, refraction at the translucent pills 22 becomes large. If light irradiated from a light emitting portion 31 is diffusion light in this manner, since irradiation angles of light are various, light irradiated from the light emitting portion 31 reaches the imaging portion 11 at any angles of the lines 35a, 35b, 35c, 35d, 35e, 35f and 35g. Hence, pixels having low brightness values showing the translucent pills 22 are not produced, outlines of the translucent pills 22 are clearly shot on the transmission image which is acquired by the imaging portion 11.

When diffusion light is used as illumination, opaque pills 21 in a medical envelope 20 are clearly shot as shown in a transmission image in FIG. 6(b). However, light passes through a transparency film of the medical envelope 20 which becomes a back ground, and light also passes through the translucent pills 22 depending upon a permeation rate thereof. Hence, brightness values of the back ground and the translucent pill 22 become almost the same. Therefore, even if the binarization processing and edge extraction processing are carried out for the shot image, it is only possible to slightly extract only the outer periphery of the translucent pill 22, and it is difficult to clearly distinguish from the translucent pill 22 the back ground. In this case, it is difficult to adjust a threshold value by binarization of the shot image, and an outline of the translucent pill 22 is frequently cut. Further, if the shot image is subjected to smoothing processing to remove other noises, the outline of the translucent pill 22 is removed like the noises. Hence, even if imaging processing is carried out, it is not possible to detect as the translucent pill 22. Here, the back ground means a region where pills do not exist in the shot image, and is a region which passes through only the transparency film.

FIG. 7 show a conceptual diagram and a shot image of transmission of a translucent pill when parallel light is used as illumination.

In FIG. 7, to emit parallel light, an illumination portion 30 includes a parallel light converting portion 32 for converting diffusion light into parallel light and also includes a light emitting portion 31.

As shown in FIG. 7(a), if light irradiated from the illumination portion 30 is parallel light, since variation of irradiation angle is small, a location through which light cannot pass is generated in the translucent pill 22. Light having an angle which is close to the irradiation angle like the line 35d reaches the imaging portion 11. However, in the case of light having the angles like the lines 35a, 35b, 35c, 35e, 35f and 35g, since irradiation light which is irradiated from the parallel light converting portion 32 does not have an angle, light which enters the imaging portion 11 becomes weak, and a brightness value of the outer periphery of the translucent pill 22 becomes low.

Hence, as shown in FIG. 7(b), a brightness value of a center of the translucent pill 22 becomes high and a brightness value of the outer periphery becomes low. Therefore, an outline of the translucent pill 22 is clearly shot on the transmission image which is acquired by the imaging portion 11.

FIG. 8 is a diagram for explaining parallel light which is irradiated from an illumination portion.

As shown in FIG. 8, out of parallel light which is irradiated from the illumination portion 30, light (lines 36a, 36g) which passes through a medical envelope is not refracted and thus, such light straightly travels. However, out of light (lines 36b to 36f) which passes through a transparent pill, light which passes through the outer periphery of the translucent pill 22 is refracted significantly. Therefore, such light does not reach the imaging portion 11, and a brightness value of the outer periphery of the translucent pill 22 is lowered. On the other hand, in the case of light which passes through a location in the vicinity of the center of the translucent pill 22, since a degree of refraction thereof is small, the imaging portion 11 receives the light and a brightness value becomes high.

Here, since a refraction index is determined by curvature of the translucent pill 22, a brightness value of the outer periphery of the translucent pill 22 becomes low irrespective of a permeation rate of the translucent pill 22. By utilizing the fact that the brightness value of the outer periphery of the translucent pill 22 is lowered by the parallel light, it is possible to clearly distinguish the translucent pill 22 and the back ground from each other, and to precisely detect the translucent pill 22.

Irradiation of parallel light is described in patent document 1.

PRIOR ART DOCUMENT

Patent Document

[PATENT DOCUMENT 1] Japanese Patent Application Laid-open No. 2008-18230

SUMMARY OF THE INVENTION

Problem to be Solved by the Invention

If parallel light is used, it is possible to clarify an outline of the translucent pill 22 as compared with a case where diffusion light is used.

However, when the translucent pill 22 exists directly below the imaging portion 11, the outline can be clarified, but when the translucent pill 22 exists at a position deviated from directly below the imaging portion 11, deviation is generated in the outline.

FIG. 9(*a*) is an explanatory diagram when the translucent pill 22 exists at the position deviated from directly below the imaging portion 11, and FIG. 9(*b*) is a shot image.

As shown in FIG. 9(*b*), when an imaging position (shooting position, hereinafter) is deviated from below the imaging portion 11 in the vertical direction, deviation is generated in the outline of the translucent pill 22, and a case where the outline cannot be recognized by this deviation is generated.

Hence, it is an object of the present invention to provide a pill inspection apparatus and a pill inspection method capable of inspecting a translucent pill irrespective of a permeation rate by obtaining a uniform outline of the translucent pill irrespective of a shooting position.

Means for Solving the Problem

A first aspect of the present invention provides a pill inspection apparatus including: an illumination portion for irradiating light to a medical envelope in which at least a translucent pill is enclosed; an imaging portion for acquiring a transmission image of the irradiated medical envelope; and an image processing portion for detecting, as the translucent pill, a pill having a brightness value of its outer periphery lower than that of its center using the transmission image, wherein the illumination portion includes a light emitting portion, and a light-collecting portion for collecting the light is provided between the light emitting portion and the medical envelope.

According to a second aspect of the invention, in the pill inspection apparatus of the first aspect, the light emitting portion emits diffusion light, and a parallel light converting portion for converting the diffusion light into parallel light is provided between the light emitting portion and the light-collecting portion.

According to a third aspect of the invention, in the pill inspection apparatus of the second aspect, the light-collecting portion is a convex lens or a Fresnel lens.

According to a fourth aspect of the invention, in the pill inspection apparatus of the any one of first to third aspects, a domical illumination portion is provided between the medical envelope and the imaging portion.

A fifth aspect of the present invention provides a pill inspection method including: a step of irradiating light to a medical envelope in which at least a translucent pill is enclosed to acquire a transmission image; a step of detecting, as the translucent pill, a pill having a brightness value of its outer periphery lower than that of its center using the transmission image; and a step of collecting the light from an illumination portion into an imaging portion.

Effect of the Invention

According to the present invention, it is possible to provide a pill inspection apparatus and a pill inspection method capable of inspecting a translucent pill irrespective of a permeation rate by obtaining a uniform outline of the translucent pill irrespective of a shooting position.

BRIEF DESCRIPTION OF THE DRAWINGS

FIG. 1 is a block diagram showing a pill inspection apparatus according to an embodiment of the present invention;

FIG. 2 is a perspective view of a parallel light converting portion used in the pill inspection apparatus;

FIG. 3(*a*) is a conceptual diagram of transmission of translucent pills when light is collected at an image unit, and FIG. 3(*b*) is a diagram showing transmission image of shot translucent pills;

FIG. 4 are conceptual diagrams of transmission of translucent pills when a domical illumination shown in FIG. 1 is provided;

FIG. 5 is a flowchart showing a method to inspect a pill using the pill inspection apparatus of the embodiment;

FIG. 6 are a conceptual diagram and a shot image of transmission of translucent pills when diffusion light is used as illumination;

FIG. 7 are a conceptual diagram and a shot image of transmission of the translucent pills when parallel light is used as illumination;

FIG. 8 is a diagram for explaining parallel light irradiated from an illumination portion; and FIG. 9 are an explanatory diagram and a shot image when the translucent pills exists at a position deviated from a location below an imaging portion in the vertical direction.

MODE FOR CARRYING OUT THE INVENTION

A pill inspection apparatus according to a first aspect of the present invention includes a light-collecting portion for collecting the light is provided between the light emitting portion and the medical envelope. According to this aspect, it is possible to inspect a translucent pill irrespective of a permeation rate by obtaining a uniform outline of the translucent pill irrespective of a shooting position.

According to a second aspect, in the pill inspection apparatus of the first aspect, the light emitting portion emits diffusion light, and a parallel light converting portion for converting the diffusion light into parallel light is provided between the light emitting portion and the light-collecting portion. According to this aspect, by collecting the parallel light after the diffusion light is converted into the parallel light, it is possible to obtain a uniform outline of the translucent pill.

According to a third aspect, in the pill inspection apparatus of the second aspect, the light-collecting portion is a convex lens or a Fresnel lens. According to this aspect, by using the Fresnel lens, it is possible to shorten a distance between an illumination portion and the medical envelope.

According to a fourth aspect, in the pill inspection apparatus of any one of the first to third aspects, a domical illumination portion is provided between the medical envelope and the imaging portion. According to this aspect, even if the domical illumination is provided, it is possible to obtain a uniform outline of the translucent pill without being influenced by the domical illumination.

A pill inspection method according to a fifth aspect of the present invention includes a step of irradiating light to a medical envelope in which at least a translucent pill is enclosed to acquire a transmission image; a step of detecting, as the translucent pill, a pill having a brightness value of its outer periphery lower than that of its center using the transmission image; and a step of collecting the light from an illumination portion into an imaging portion. According to this aspect, it is possible to inspect a translucent pill irrespective of a permeation rate by obtaining a uniform outline of the translucent pill irrespective of a shooting position.

Embodiment

An embodiment of the present invention will be described together with the drawings.

FIG. 1 is a block diagram showing a pill inspection apparatus according to the embodiment of the invention, and FIG. 2 is a perspective view of a parallel light converting portion used in the pill inspection apparatus. The same reference symbols are allocated to the same constituent elements, and explanation thereof will be omitted in some cases. For ease of comprehension, the drawings are illustrated schematically mainly based on the respective constituent elements.

The pill inspection apparatus inspects whether appropriate pills are enclosed in a medical envelope 20 in accordance with prescription. Pills according to the prescription are enclosed in the medical envelope 20 by a pill packaging machine (not shown).

As shown in FIG. 1, to carry out an inspection operation, the pill inspection apparatus acquires an image of the medical envelope 20 including an opaque pill and a translucent pill by an imaging portion 11. An image processing portion 12 counts the number of pills based on the image of the medical envelope 20 acquired by the imaging portion 11, brings the counted number and the number of pills described in the prescription into check, and determines whether the pills are appropriately enclosed in the medical envelope 20. A camera portion is used as the imaging portion 11 for example. The imaging portion 11 acquires a transmission image of the medical envelope 20 into which light is irradiated from an illumination portion 30. The imaging portion 11 includes an image element and a lens. A mounting table 13 conveys the medical envelope 20.

The mounting table 13 includes a guide portion 15 provided on an end of a mounting surface. The medical envelope 20 is mounted on the mounting surface. The mounting table 13 also includes a transparent plate 16 through which light of the illumination portion 30 passes. The guide portion 15 is provided therein with a drive roller and a guide roller (both not shown). An end of the medical envelope 20 is sandwiched between the drive roller and the guide roller, and the drive roller is rotated. According to this, the medical envelope 20 is moved along the guide portion 15. The mounting table 13 is placed between the imaging portion 11 and the illumination portion 30.

The imaging portion 11 is opposed to the mounting surface of the mounting table 13 on which the medical envelope 20 is mounted, and the imaging portion 11 is located above the illumination portion 30. The imaging portion 11 shots, from above, an image of the medical envelope 20 into which light is irradiated from below the mounting surface, and acquires a transmission image of the medical envelope 20.

A display portion 14 is connected to the image processing portion 12, and displays an image of pills detected by the image processing portion 12. Hence, a tester (examiner) can visually inspects using the display portion 14.

A domical illumination portion 40 is provided below the imaging portion 11 and above the transparent plate 16. The medical envelope 20 is irradiated with light from the domical illumination portion 40, and the medical envelope 20 is shot by the camera unit 11.

The illumination portion 30 irradiates, with light, the medical envelope 20 enclosing the translucent pills 22 and the opaque pills 21. The illumination portion 30 includes a light emitting portion 31 which emits diffusion light, a parallel light converting portion 32 which converts diffusion light into parallel light, and a light-collecting portion 33 which collects parallel light. A LED which is mounted to a diffusion plate is used as the light emitting portion 31. A convex lens or a Fresnel lens is used as the light-collecting portion 33.

A distance from the imaging portion 11 to the light-collecting portion 33 is equal to a focal distance of the light-collecting portion 33. In this embodiment, light is collected by the light-collecting portion 33 after diffusion light is converted into the parallel light by the parallel light converting portion 32. Alternatively, light diffused from a single light source may be collected. In this case, the distance from the imaging portion 11 to the light-collecting portion 33 is equal to a half of the focal distance of the light-collecting portion 33.

The opaque pills 21 which block light and translucent pills 22 through which light passes with a constant transmission factor are enclosed in the medical envelope 20.

The opaque pill 21 blocks light. Many of general pills are opaque pills 21.

Each of the translucent pills 22 encloses medicinal solution with a transparent film. Hence a degree of transmission of light differs depending upon a degree of transmission of the medicinal solution. Since the translucent pill 22 encloses the medicinal solution, the translucent pill 22 has a roundish shape such as a ball shape, a spheroid shape and a capsule shape.

The medical envelope 20 includes a pasted board region 20a having a permeation rate lower than that of the transparency film so that information is printed. The medical envelope 20 also includes non-pasted board regions 20b of transparency films.

As shown in FIG. 1, the imaging portion 11 acquires a transmission image of the medical envelope 20. The transmission image includes translucent pills 22 having low brightness values of an obtained outer periphery. Utilizing the fact that the brightness value of the outer periphery of the translucent pill 22 becomes low, the image processing portion 12 detects an outline of the translucent pill 22 from the transmission image of the medical envelope 20.

After the pill inspection apparatus acquires the transmission image of the medical envelope 20 by the imaging portion 11, the pill inspection apparatus detects translucent pills 22 included in the transmission image of the medical envelope 20 and detects opaque pills 21 included in the transmission image of the medical envelope 20. The number of pills of the prescription and a sum of the number of detected translucent pills 22 and the number of detected opaque pills 21 are compared with each other, and it is determined whether an appropriate number of pills exist in the medical envelope 20, thereby checking the number of pills. The pill inspection apparatus inspects the pills in such a method. Details of the checking operation of the number of pills carried out by the pill inspection apparatus will be described based on a flowchart shown in FIG. 5.

As shown in FIG. 2, the parallel light converting portion 32 converts diffusion light into parallel light. The parallel light converting portion 32 is formed of laminated bodies 32c and 32d which are formed by laminating, on one another, transmission bands 32a through which visible light passes and absorption belts 32b which absorb visible light. Here, the laminated body 32c and the laminated body 32d are superposed on each other such that a laminating direction of the transmission band 32a and the absorption belt 32b of the laminated body 32c and a laminating direction of the transmission band 32a and the absorption belt 32b of the laminated body 32d intersect with each other at right angles. Out of diffusion light which is emitted from the light emitting portion 31, only light which enters at a predetermined incident angle passes through the parallel light converting portion 32, and the parallel light converting portion 32 absorbs light which enters at incident angles other than the former incident angle. Since only the light having the predetermined incident angle passes through the parallel light converting portion 32, light radiated from the parallel light converting portion 32 becomes parallel light. This parallel light is collected by the light-collecting portion 33. A louvered film can be used as the parallel light converting portion 32.

Next, a reason why the translucent pills 22 can precisely be detected using the transmission image of the medical envelope 20 acquired by the imaging portion 11 will be described.

FIG. 3(a) is a conceptual diagram of transmission of the translucent pills 22 when light is collected at the imaging portion 11, and FIG. 3(b) is a diagram showing transmission image of the shot translucent pills 22.

FIG. 3(a) shows a translucent pill 22A located directly below the imaging portion 11 in the vertical direction, and a translucent pill 22B located at a position deviated from directly below the imaging portion 11 in the vertical direction.

Each of the translucent pills 22 has a roundish shape. Hence, the translucent pill 22 plays a role as a lens, light passing through the outer periphery of the translucent pill 22 is refracted, and light passing through a center thereof straightly travels.

At the translucent pill 22A located directly below the imaging portion 11 in the vertical direction, light passing through the center reaches the imaging portion 11 and its brightness value becomes high like the parallel light, but light passing through the outer periphery which enters the imaging portion 11 becomes weak, and its brightness value becomes low. The translucent pill 22 has a roundish shape such as a ball shape, a spheroid shape and a capsule shape, and a refraction index thereof is gradually varied from the outer periphery toward the center of the translucent pill 22. Therefore, the outer periphery where the brightness value becomes low has a width of a certain level. A shape of a region having the low brightness value matches with an outline shape of the translucent pill 22. Therefore, image processing for comparing the shapes, e.g., image processing such as pattern matching becomes easy.

At the translucent pill 22B located at the position deviated from directly below the imaging portion 11 in the vertical direction, its outline is deviated as shown in FIG. 9 in the case of the parallel light. In this embodiment, however, all of light passing through the translucent pill 22B travels toward the imaging portion 11, its outline is not deviated, light passing through the center reaches the imaging portion 11, a brightness value thereof becomes high, light passing through the outer periphery which enters the imaging portion 11 becomes weak and its brightness value becomes low.

FIG. 4 are conceptual diagrams of transmission of translucent pills when the domical illumination shown in FIG. 1 is provided, FIG. 4(a) shows the present embodiment where light is collected by the imaging portion and FIG. 4(b) shows a transmission image of the translucent pills. FIG. 4(c) shows a comparative example using diffusion light, and FIG. 4(d) shows a comparative example using parallel light. In the drawings, thickness of arrows shows intensity of light.

In FIG. 4(a), since light is collected at the imaging portion 11 by the light-collecting portion 33, light from the light-collecting portion 33 is not reflected by the domical illumination portion 40 so often. Since the amount of light reflected from the domical illumination portion 40 is small, a feature of illumination using parallel light, i.e., a feature that a brightness value of the center of the translucent pill 22 is high and a brightness value of the outer periphery is low is emphasized.

On the other hand, in the comparative example using diffusion light shown in FIG. 4(c) and in the comparative example using parallel light shown in FIG. 4(d), since a periphery of the domical illumination portion 40 is illuminated with strong light, such light is reflected by the domical illumination portion 40. Hence, translucent pill 22 is also illuminated with such the reflection light from the domical illumination portion 40, and a brightness value of the entire translucent pill 22 becomes high. According to this, the feature of illumination using parallel light, i.e., the feature that the brightness value of the center of the translucent pill 22 is high and the brightness value of the outer periphery is low becomes weak due to the fact that the brightness value of the entire translucent pill 22 becomes high, and it becomes difficult to detect the translucent pill 22.

In the case of the transmission image of the present embodiment obtained by collecting light at the imaging portion 11, an outline of the opaque pill 21 located at a position away from directly below the imaging portion 11 in the vertical direction is also clear, and the outline of the outer periphery of the translucent pill 22 is also uniform and clear. Hence, the image processing portion 12 can easily detect the outlines of the opaque pill 21 and the translucent pill 22 by the transmission image. In this embodiment, detection of the translucent pill 22 is carried out by pattern matching between the transmission image and sample images of the translucent pills 22, and the number of detected translucent pills 22 is calculated. Further, since images of the opaque pill 21 and the translucent pill 22 are different from each other due to a difference in the transmission factor, it is possible to clearly distinguish between the opaque pill 21 and the translucent pill 22 in this embodiment.

Before the pattern matching between the transmission image and the sample image of the translucent pill 22 is carried out, the image processing portion 12 carries out a thinning operation and edge extraction by an extreme value with respect to the transmission image, and detects an outline of the translucent pill 22 by the transmission image. By carrying out the thinning operation and edge extraction by the extreme value with respect to the transmission image in this manner, noise is removed, and the outline of the pill is clarified. Here, the brightness value of the outer periphery of the translucent pill 22 is low and its width is constant as described above. However, if parallel light in which light is not collected is used, a refraction index of light which reaches the imaging portion 11 is changed depending upon an attitude of the pill and a relative position from the imaging portion 11. Hence, even if a kind of pills is the same, a wide portion and a narrow portion of the outer periphery having the low brightness value are generated. By collecting parallel light, influence of a relative position from the imaging portion 11 is reduced, and a width of the outer periphery having a low brightness value becomes uniform.

At the time of detection of the translucent pill 22 such as the pattern matching, since the width of the outer periphery becomes uniform, it is possible to minimize adverse influence such as cut of the outline of the translucent pill 22. Since the refraction index of the translucent pill 22 from the center to the outer periphery is changed in stages, the brightness value of the outer periphery of the translucent pill 22 is changed from the center in stages. Concerning the outermost side of the translucent pill 22, however, the brightness value is changed extremely. Therefore, when the transmission image is subjected to the differential processing to extract an edge, the thinning operation for leaving only an extreme value having a large changing amount is carried out. According to this, it is possible to leave only the outermost outer periphery. Concerning the outermost outer periphery, i.e., the outline of the translucent pill 22, since a size of the outline is also determined by a size of each of the pills, stable pattern matching which is not influence by a position and an attitude of the pill can be realized.

Here, the medical envelope 20 includes a pasted board region 20a having a permeation rate lower than that of the transparency film for printing, and a non-pasted board region 20b of the transparency film. In the pasted board region 20a, if the translucent pill 22 exists on a boundary between the pasted board region 20a and the non-pasted board region 20b for weakening light of the illumination portion 30, a brightness value of one translucent pill 22 differs on the side of the pasted board region 20a and on the side of the non-pasted board region 20b. As a result, if attempt is made to detect the outline of the translucent pill 22, the outline is erroneously detected in some cases. Hence, when the outline of the translucent pill 22 is detected by the transmission image of the medical envelope 20, the transmission image of the medical envelope 20 is divided into the pasted board region 20a and the non-pasted board region 20b, and the outline of the translucent pill 22 is detected using two threshold values, i.e., a pasted board region threshold value for detecting the outline of the translucent pill 22 by the pasted board region 20a, and a non-pasted board region threshold value for detecting the outline of the translucent pill 22 by the non-pasted board region 20b.

If the image processing portion 12 uses the two threshold values for detecting the outline of the translucent pill 22 in this manner, even if the translucent pills 22 exist in the pasted board region 20a and the non-pasted board region 20b, the translucent pills 22 can be detected as one pill.

When the image processing portion 12 extracts the edge, the image processing portion 12 recognizes the longest line and the second longest as a boundary line of the pasted board region 20a, and recognizes a space between these two lines as the pasted board region 20a. Since the pasted board region 20a is formed as a wide range so that it is easy to notice, it is possible to easily discriminate the pasted board region 20a by detecting the longest line and the second longest line.

Next, a pill inspection method which is carried out by using the above-described pill inspection apparatus will be described.

FIG. 5 is a flowchart showing the pill inspection method using the pill inspection apparatus of the present embodiment.

First, the pill inspection apparatus collects parallel light from the parallel light converting portion 32 at the imaging portion 11 by the light-collecting portion 33, the pill inspection apparatus irradiates the light to the medical envelope 20 including the translucent pill 22, and acquires the transmission image including the translucent pill 22 having a low brightness value of the outer periphery (step S01). Here, the transmission image includes an image of the opaque pill 21 and an image of the translucent pill 22.

Next, the pill inspection apparatus detects the translucent pills 22 by the transmission image. To calculate a threshold value for detecting the translucent pill 22, the pill inspection apparatus carries out the edge extraction processing by a Canny method for the transmission image of the medical envelope 20. Straight lines are extracted by haugh conversion from the edge image obtained by the edge extraction processing. Out of straight lines obtained by the straight line extraction, the longest two straight lines extending in the longitudinal direction of the pasted board region 20a are combined as one group, and an interior thereof is extracted as the pasted board region 20a. A mode value of the pasted board region 20a and a mode value of a pixel other than the pasted board region 20a are compared with each other, and a threshold value for extracting the edge of step S03 is calculated by the ratio (step S02). To clarify the outlines of the opaque pill 21 and the translucent pill 22, the pill inspection apparatus carries out the thinning operation for the transmission image of the medical envelope 20 by the edge extraction by the Canny method and the extreme value (step S03). In step S03, the translucent pills 22 are detected by pattern matching with respect to the sample image from the edge extraction image which is subjected to the edge extraction. More specifically, a sample image of only the outline is prepared by the image processing portion 12 from a size of the translucent pill 22 described in a prescription, pattern matching is carried out between the sample image and the edge image of the transmission image of the medical envelope 20, and the translucent pills 22 are detected from the transmission image. The number of the detected translucent pills 22 is calculated as the number of the translucent pills 22 (step S04). From step S01 to step S04, the number of translucent pills 22 enclosed in the medical envelope 20 can precisely be calculated.

Next, the pill inspection apparatus detects the opaque pills 21. First, the translucent pills 22 are removed from the transmission image of the medical envelope 20 (step S05). Next, the transmission image from which the translucent pills 22 are removed is binarized (step S06). The number of opaque pills 21 is calculated from the binarized transmission image by corner extraction. Since the opaque pills 21 are left in the transmission image of the binarized medical envelope 20, the number of calculated pills becomes equal to the number of opaque pills 21 (step S07).

Next, the number of pills of the prescription and a sum of the number of the detected translucent pills 22 and the number of the detected opaque pills 21 are compared with each other, and it is determined whether an appropriate number of pills exist in the medical envelope 20 (step S08). By determining whether the sum of the number of translucent pills 22 calculated in step S04 and the number of opaque pills 21 calculated in step S07 is the appropriate number, the number of pills is checked. From step S01 to step S08, the total number of pills enclosed in the medical envelope 20 is calculated.

In this manner, the pill inspection apparatus can inspect the translucent pills 22 irrespective of the permeation rate of the translucent pills 22.

In the above-described pill inspection apparatus, to irradiate light to the medical envelope 20, the light emitting portion 31, the parallel light converting portion 32 and the light-collecting portion 33 are combined with each other to form the illumination portion 30. However, this is only one example, and the light-collecting portion 33 may be formed by using Fresnel lens as the transparent plate. It is possible to use a honeycomb board as the parallel light converting portion 32 other than the louvered film. It is possible to irradiate parallel light from the light emitting portion 31 at a position away from the medical envelope 20 more than 1 m without using the parallel light converting portion 32.

If attempt is made to detect the translucent pill 22 by pattern matching from the transmission image, when there exist an opaque pill 21 and a translucent pill 22 having similar shape of their outer peripheries, the opaque pill 21 is detected as the translucent pill 22 in some cases. Hence, to precisely detect the translucent pill 22, it is preferable that the image processing portion 12 detects, as the translucent pill 22, a pill having a pixel having a high brightness value at a center of the detected pill in the transmission image.

If the pill inspection apparatus in this embodiment is used, a pixel having a high brightness value necessarily exits at the center of the translucent pill 22. Hence, even if a shape of the opaque pill 21 and a shape of a sample image of the translucent pill 22 are the same, if a pixel having a high brightness value does not exist at the center of the pill, the pill inspection apparatus determines this pill as the opaque pill 21, and if a pixel having a high brightness value exists at the center of the pill, the pill inspection apparatus may determine this pill as the translucent pill 22.

According to this, it is possible to detect the opaque pill 21 and the translucent pill 22 distinctively.

INDUSTRIAL APPLICABILITY

The pill inspection apparatus and the pill inspection method of the present invention are useful in a pharmacy and a hospital where a preparation operation of a medicine must be carried out.

EXPLANATION OF SYMBOLS

11 imaging portion
12 image processing portion
13 mounting table
14 display portion
15 guide portion
16 transparent plate
20 medical envelope
20a pasted board region
20b non-pasted board region
21 opaque pill
22 translucent pill
30 illumination portion
31 light emitting portion
32 parallel light converting portion
33 light-collecting portion
40 domical illumination portion

The invention claimed is:

1. A pill inspection apparatus comprising:
an illumination portion for irradiating light to a medical envelope in which at least a translucent pill is enclosed, the translucent pill having a roundish shape that operates as a lens having a refraction index that varies from an outer periphery toward a center of the translucent pill with light passing through the center traveling more straightly than through an outer periphery;
an imaging portion for acquiring a transmission image of the irradiated medical envelope; and
an image processing portion for detecting, as the translucent pill, a pill having a brightness value of its outer periphery lower than that of its center using the transmission image, wherein
the illumination portion includes a light emitting portion, and a light-collecting portion for focusing the light toward the imaging portion is provided between the light emitting portion and the medical envelope such as to improve inspection irrespective of a shooting position, wherein whether the translucent pill is directly below the imaging portion in a vertical direction or deviated from directly below the imaging portion laterally to a side of the imaging portion, the light-collecting portion directs light emitted by said light emitting portion through the center of the translucent pill substantially straightly to the imaging portion with a high brightness, while light passing through the outer periphery of the translucent pill which enters the imaging portion has a low brightness, whereby the combination of the light-collecting portion and the translucent pill having a roundish shape that operates as a lens enhances inspection of the translucent pill regardless of position.

2. The pill inspection apparatus according to claim 1, wherein the light emitting portion emits diffusion light, and a parallel light converting portion for converting the diffusion light into parallel light is provided between the light emitting portion and the light-collecting portion.

3. The pill inspection apparatus according to claim 2, wherein the light-collecting portion is a convex lens or a Fresnel lens.

4. The pill inspection apparatus according to claim 1, wherein a domical illumination portion is provided between the medical envelope and the imaging portion.

5. A pill inspection method comprising:
a step of irradiating light from a light emitting portion of an illumination portion to a medical envelope in which at least a translucent pill is enclosed to acquire a transmission image, the translucent pill having a roundish shape operating as a lens wherein the refraction index varies from an outer periphery toward a center of the translucent pill with light passing through the center traveling more straightly than through an outer periphery;
a step of detecting, as the translucent pill, a pill having a brightness value of its outer periphery lower than that of its center using the transmission image; and
a step of collecting the light from the light emitting portion of the illumination portion including focusing the light into an imaging portion with a light-collecting portion such as to improve inspection irrespective of a shooting position, including whether the translucent pill is directly below the imaging portion in a vertical direction or deviated from directly below the imaging portion laterally to a side of the imaging portion, the light-collecting portion directs light emitted by said light emitting portion through the center of the translucent pill substantially straightly to the imaging portion with a high brightness, while light passing through the outer periphery of the translucent pill which enters the imaging portion has a low brightness, whereby the combination of the light-collecting portion and the translucent pill having a roundish shape that operates as a lens enhances inspection of the translucent pill regardless of position.

6. The pill inspection apparatus according to claim 2, wherein a domical illumination portion is provided between the medical envelope and the imaging portion.

7. The pill inspection apparatus according to claim 3, wherein a domical illumination portion is provided between the medical envelope and the imaging portion.

8. The pill inspection apparatus according to claim 1, wherein the light-collecting portion converges the light inwardly toward the imaging portion.

9. The pill inspection method of claim 5, wherein said step of collecting the light from an illumination portion includes converging the light inwardly toward the imaging portion.

10. The pill inspection apparatus according to claim 1, wherein the light-collecting portion is a convex lens or a Fresnel lens that converges the light inwardly toward the imaging portion.

11. The pill inspection method of claim 5, wherein said step of collecting the light from an illumination portion includes providing a light-collecting portion with a convex lens or a Fresnel lens that converges the light inwardly toward the imaging portion.

12. The pill inspection apparatus according to claim 1, wherein a distance from the imaging portion to the light-collecting portion is based on a focal distance of the light-collecting portion.

13. The pill inspection method of claim 5, further including setting a distance from the imaging portion to a light-collecting portion based on a focal distance of the light-collecting portion.

14. The pill inspection method of claim 5, further including providing said at least a translucent pill along with a plurality of additional pills within said medical envelope, and said steps of collecting light and detecting concurrently inspecting said plurality of additional pills within said medical envelope.

15. The pill inspection method of claim 14, wherein said plurality of additional pills includes at least one opaque pill.

16. The pill inspection method of claim 15, further including counting a number of pills within the medical envelope based on said detecting.

* * * * *